United States Patent [19]

Losch et al.

[11] Patent Number: 5,082,944
[45] Date of Patent: Jan. 21, 1992

[54] PRODUCTION OF PYRIDINE-3-SULFONIC ACID

[75] Inventors: Rolf Losch, Ketsch; Winfried Orth, Hassloch/Pflaz; Wolfgang Weiss, Neckarhausen; Hans W. Kleffner, Battenberg, all of Fed. Rep. of Germany

[73] Assignee: Rutgerswerke AG, Fed. Rep. of Germany

[21] Appl. No.: 606,089

[22] Filed: Oct. 31, 1990

[51] Int. Cl.$^5$ ............... C07D 213/71; C07D 213/62
[52] U.S. Cl. ............................. 546/294; 546/345
[58] Field of Search ............................. 546/294

[56] References Cited

PUBLICATIONS

Chem. Abstracts, vol. 57(3) pp. 3405-3407 Aug. 6, 1962.
Chem. Abstracts, vol. 66 (9) abst. No. 37,736h, Feb. 27, 1967.
Chem. Abstracts, vol. 79 (15), abst. No. No. 91937f, Oct. 15, 1973.

*Primary Examiner*—Alan L. Rotman
*Attorney, Agent, or Firm*—Bierman and Muserlian

[57] ABSTRACT

A method for the production of heavy metal-free pyridine-3-sulfonic acid by oxidation of 3-chloro-pyridine to 3-chloro-pyridine-N-oxide, substitution of the chlorine through a sulfonic acid group, and subsequent reduction to pyridine-3-sulfonic acid. The method can be carried out using raw 3-chloropyridine-N-oxide and direct further reaction of the pyridine-3-sulfonic acid-N-oxide in the presence of Raney nickel in an alkaline solution.

3 Claims, No Drawings

PRODUCTION OF PYRIDINE-3-SULFONIC ACID

STATE OF THE ART 3-pyridine sulfonic acid is a compound much in demand in electroplating as it functions to improve the precipitation behavior of electropolating baths. Pyridine-3-sulfonic acid is also used as on intermediate product in the production of sulfonamides and other pharmaceutical agents as well as also for water-soluble reactive dyestuff.

O. Fischer (Ber., Vol. 15, 62 (1882) described already in 1882 the sulfonation of pyridine with concentrated sulfuric acid at 300° to 350° C. and after a reaction time of 24 hours, pyridine-3-sulfonic acid could be isolated with a yield of 50%. Subsequent investigations had the goal to produce the acid under milder reaction conditions in a shorter reaction time with a higher yield.

Elvain et al found that the reaction temperature could be lowered to 230° C. by the addition of mercuric sulfate and that the yield could be increased by approximately 20% [Journal of American Chemical Society, Vol. 65, page 2233 (1943)].

The industrial method currently used for the production of pyridine-3-sulfonic acid rests essentially on the investigations of Elvain et al.

Judged under aspects of chemical engineering and ecology, this synthesis method has considerable drawbacks. High energy costs arise due to the high reaction temperatures which must be maintained over a long reaction time. Simultaneously at the high temperature, corrosive $SO_3$ vapors are released from the concentrated sulfuric acid solution (fuming sulfuric acid) and therefore, production facilities for the method must be of very high quality and resistant under these aggressive conditions.

The mercuric sulfate used as catalyst must be removed in a complicated manner from the product since, on the one hand, in the pharmaceutical industry only extremely pure products can be used, and, on the other hand, as a toxic heavy metal salt, it engenders considerable disposal problems even in traces with use in electropolating.

OBJECTS OF THE INVENTION

It is an object of the invention to provide an enviromentally safe method for the preparation of pyridine-3-sulfonic acid free of heavy metals, particularly mercury, under mild conditions at low temperatures with increased yields.

This and other objects and advantages of the invention will become obvious from the following detailed description.

THE INVENTION

The novel method of the invention for the prepartion of pyridine-3-sulfonic acid comprises oxidizing 3-chloro-pyridine to form 3-chloro-pyridine-N-oxide, reacting the latter with a sulfonating agent to form 3-sulfonic acid-pyridine-N-oxide and catalytically reducing the latter to form pyridine-3-sulfonic acid.

3-chloro-pyridine for reasons of economy is used as the starting compound for the synthesis of 3-pyridine-sulfonic acid which accumulates as undesired by-product in the synthesis of 2-chloro-pyridine which at this time cannot be used for other purposes and must therefore be disposed of. Conversion of 3-chloro-pyridine to 3-pyridine-sulfonic acid accordingly makes the method for the production of 2-chloro-pyridine more cost-effective since the disposal becomes unnecessary. On the other hand, 3-chloro-pyridine is an inexpensive starting compound for the production of 3-pyridine sulfonic acid. Substitution of chlorine in 3-chloro-pyridine with a sulfonic acid group however is not possible.

In the method of the invention therefore, 3-chloro-pyridine is converted to the N-oxide in a first method step and the sulfonation takes place subsequently according to methods known per se. The pyridine-3-sulfonic acid-N-oxide must then be reduced to pyridine-3-sulfonic acid in a further method step, preferably by a hydrogenation reaction.

To be able to carry out the preparation of pyridine-3-sulfonic acid with minimum expenditures and high yield, a reduction method had to be found in which the non-purified pyridine-3-sulfonic acid-N-oxide is converted directly. Known reduction reactions for pyridine-N-oxide are with elemental sulfur, thiourea, sodium dithionite, sodium hydrogen sulfite, sodium sulfite, and phosphorous trichloride. However, these reactions are not possible since these chemical reduction reactions do not lead to complete conversion and resulting by-products must be removed in a complicated manner.

Another possibility for removing the nitrogen-bound oxygen is by catalytic hydrogenation, but rather unfavorable starting conditions are present in the solution from the production of the pyridine-3-sulfonic acid-N-oxide since further reaction partners present in the solution act as catalyst poisons and by-products resulting in the sulfonation have a disturbing influence. Hydrogenation attempts with purified pyridine-3-sulfonic acid-N-oxide on nobel metal catalysts such as platinum and palladium show a selectivity which is too small. The aromatic nucleus is hydrogenated immediately and piperidine-3-sulfonic acid is produced exclusively.

Among the cataysts which can be used for hydrogenation on an industrial scale is Raney nickel. For hydrogenation, most often higher temperatures and pressures are necessary. Raney nickel is primarily used for saturating aromatic systems and for the hydrogenolysis of organic sulfur compounds (cf. Houben-Weyl, Methoden der organischen Chemie, Vol. 4, Reduction I, Georg Thieme Verlag, Stuttgart (1980), page 21). These reactions are primarily carried out in an alcoholic solution after the Raney nickel has been washed with anhydrous alcohol, for example methanol. In a hot alkaline solution, aromatic sulfonic acids are desulfonated in the presence of Raney nickel (in: March, Jerry; Advanced Organic Chemistry, Reactions, Mechanisms, and Structure, 3rd Ed., John Wiley & Sons (1985), page 509).

However, it was surprisingly found that in an alkaline alcohol/water mixture, the purified sodium salt of pyridine-3-sulfonic acid-N-oxide can be selectively hydrogenated to pyridine-3-sulfonic acid with the retention of the aromatic nucleus. It is a further advantage that this hydrogenation takes place under relatively mild conditions. Moreover, it was found that this hydrogenation can be carried out under somewhat harsher conditions also in basic aqueous solutions without addition of alcohol. Under these conditions, only the N—O bond is hydrogenated while the sulfonic acid group is not attacked.

Since the purification of pyridine-3-sulfonic acid-N-oxide is rather complicated, it was the goal to simplify the method so that the N-oxide can be used in the non-purified state i.e., the reaction solution after the sulfonation of the 3-chloro-pyridine-N-oxide can be mixed with the hydrogenation catalyst so that the hydrogenation can be carried out without further intermediate steps. The solution resulting from the production of the sulfonic acid offers unfavorable conditions for the catalytic hydrogenation since sulfite ions are present and accumulated by-products act as catalyst poisons.

It has been found that through the addition of hydrochloric acid and the removal of $SO_2$ achieved thereby, a raw solution results which can be used for the hydrogenation. The reaction liquid is made alkaline by the addition of sodium hydroxide and is hydrogenated in the presence of Raney nickel. At 100° C. and 7 bars for example, the hydrogen uptake lasts 6 to 8 hours compared to 3 hours with purified pyridine-3-sulfonic acid-N-oxide.

But counter to all expectations, hydrogenation can also take place without removing the sulfitions After the addition of NaOH, hydrogenation under the same exemplary conditions takes 16 hours. Consequently, it is also possible to avoid the purification of pyridine-3-sulfonic acid-N-oxide and to ensure an economic combination of the method steps. Through the discovered method, heavy metal-free pyridine-3-sulfonic acid can be produced on an industrial scale.

3-chloro-pyridine is dissolved in a manner known per se in solvents, particularly in acetic acid and is oxidized with an oxidation agent at temperatures in the range of from room temperature to approximately 100° C. to form 3-chloro-pyridine-N-oxide. The 3-chloro-pyridine-N-oxide separated out with the aid of solvents or inorganic or organic extraction means or by means of distillation by conventional methods is converted in a manner known per se with known sulfonation means, particularly with alkali metal sulfite in the presence of water at increased temperatures (50° to 170° C. depending on the activity of the sulfonation means) to form pyridine-3-sulfonic acid-N-oxide with a conversion of up to 83%.

If the sulfonation is carried out with alkali metal sulfite, the resulting reaction solution of pyridine-3-sulfonic acid-N-oxide can be treated with an acid, preferably hydrochloric acid to drive $SO_2$ out of the solution. The salts precipitated therein are filtered off and the reaction solution is concentrated, made alkaline with sodium hydroxide, mixed with 3 to 9.5 g of Raney nickel for each 100 g of pyridine-3-sulfonic acid-N-oxide, and hydrogenated at 80° to 120° C. and 5 bars. Hydrogenation is continued until no further hydrogen uptake is detected which is achieved after approximately 8 to 12 hours.

A second reaction variant consists in not removing $SO_2$ from the reaction solution and to make basic the liquid resulting from the reaction of alkali sulfite and 3-chloro-pyridine-oxide directly with sodium hydroxide and to mix it with Raney nickel. Under otherwise identical conditions, the hydrogenation is extended to 15 to 20 hours. By increasing the catalyst concentration to 8 to 15 g of Raney nickel for each 100 g of pyridine-3-sulfonic acid-N-oxide, the hydrogenation time is shortened to approximately 4 to 7 hours. After complete hydrogenation, the separation of the reaction product is carried out using measures known per se such as precipitation, filtration, extraction, and crystallization.

The preferred purification method comprises the removal of sulfite still present by acidification of a pyridine-3-sulfonic acid solution, the precipitation of sodium chloride formed through concentration, and addition of concentrated hydrochloric acid and filtering. Then, the mother liquor is concentrated to a high degree. With toluol as an entraining means, the residual water is distilled off. Through the addition of isopropanol to the cooled suspension, the product is precipitated and the residual water is removed. Crystallization from hot water and/or low molecular weight alcohols subsequently takes place to obtain pyridine-3-sulfonic acid with a yield of 75 to 80% and with a purity of approximately 99% and a $SO_2$ ash content of 0.1%.

In the following examples, there are described several preferred embodiments to illustrate the invention. However, it is to be understood that the invention is not intended to be limited to the specific embodiments.

EXAMPLE 1

75 g of hydrogen peroxide (70% by weight) were added to 113.5 g of chloro-pyridine and 250 ml of acetic acid dropwise at 80° C. over a period of 3 hours and the mixture was stirred for 5 hours at 80° C. After the oxidation agent was removed by addition of sodium sulfite solution, acetic acid/water was distilled in the water jet vacuum until the liquid phase temperature had risen to 80° C. The solution was cooled and while cooling, 157 ml of water and 334 g of sodium hydroxide (50% by weight) were added at 50° C. The product phase separating was taken up in 167 ml of toluol. (If three phases are formed, additional sodium hydroxide had to be added). After the phase separation, the alkaline phase was stirred with 167 ml of toluol and the combined organic phases were distilled to remove toluol in a manner known per se to obtain a yield of 98 to 99% of 3-chloro-pyridine-N-oxide.

Analysis: content (product): 98 to 99%. $SO_4$: 0.2 to 0.5%. DC: 4 to 5 components.

EXAMPLE 2

129 g of 3-chloro-pyridine-N-oxide from Example 1, 252 g of sodium sulfite and 700 ml of distilled water were stirred for 17 hours at 145° C. and after the reaction, the water was largely distilled off and the mixture was acidified at 70° C. with 500 ml of concentrated hydrochloric acid. The suspension was stirred for one half hour and the pyridine-3-sulfonic acid-N-oxide was recovered in a manner known per se through crystallization and drying for a yield of pyridine-3-sulfonic acid-N-oxide of 76 to 80% of the theoretical melting at 247° C.

Analysis: Content: 99.5%. $SO_4$ ash: 0.1%.

EXAMPLE 3

51 g (0.29 mol) of pyridine-3-sulfonic acid-N-oxide were dissolved in 200 ml of $H_2O$ and the solution was made alkaline with 25 g of sodium hydroxide (50 weight %) and mixed with 5 g of Raney nickel. This reaction solution was heated to 95° C. in an autoclave and hydrogenated at 7 bars. The hydrogenation was completed after 3 hours and the catalyst was drawn off and the mother liquor concentrated to dryness. The residue was dissolved in 140 ml of isopropanol and 150 ml of concentrated hydrochloric acid and 4 g of sodium chloride and 4 g of activated charcoal were added. After stirring for 1 hour, the suspension was drawn off and mixed with 240 ml of isopropanol. Pyridine-3-sulfonic acid prepcipitated in the form of white crystalline platelets with a chloride content of 0.06%.

EXAMPLE 4

252 g of sodium sulfite were dissolved in the absence of oxygen in 700 ml of water and then 129.6 g of 3-chloro-pyridine-N-oxide from Example 1 were added and the mixture was heated to 145° C. in the autoclave. The reaction mixture was heated for 17 hours at 145° C. (during the reaction, a pressure of 4 to 5 bars resulted). After completion of the reaction, the mixture was cooled to 60° C. and to the cooled solution were added 35 ml of ethanol, 35 g of sodium hydroxide and under a nitrogen atmosphere, 14 g of Raney nickel (moist). The suspension was heated to 100° to 110° C. and at this temperature, hydrogen was pressed on with 7 bars and hydrogenation was carried out for 6 hours. After the hydrogenation, cooling to 70° C. took place and the catalyst was drawn off. The mixture was washed with water and one half of the volume of the liquid was distilled off in vacuo. Then at 70° C., 250 ml of concentrated hydrochloric acid were added carefully and the solution was concentrated to the limit of stirrability 500 ml of hydrochloric acid were added and the solution was stirred for 1 hour at 40° C. and then filtered. Subsequent washing with hydrochloric acid took place and hydrochloric acid/water was largely distilled off in vacuo from the mother liquor and residues of water were removed through azeotropic distillation by addition of 420 ml of toluol removed.

The remaining suspension of pyridine-3-sulfonic acid in toluol was cooled to 80° C. and mixed with 500 ml of isopropanol. Then, cooling was continued to approximately 20° C. and stirring was continued for 2 hours at this temperature. The suspension was filtered and the sulfonic acid was washed with isopropanol. The sulfonic acid was dissolved in 130 ml of distilled water and after cooling to 70° C., 500 ml of ethanol were added. At 20° C., the pyridine-3-sulfonic acid was filtered and washed with ethanol to obtain a yield of 75 to 80% of the theoretical amount of product.

Analysis: Content (from acid number): appr. 99%. $SO_4$ ash: 0.1%.

EXAMPLE 5

18.7 kg of sodium bisulfite were dissolved in 55.8 liters of water and the pH was adjusted to a pH of 9 to 9.5 with 14.4 kg of sodium hydroxide. To the solution were added 11.7 kg of raw 3-chloro-pyridine-N-oxide and the mixture was heated in an autoclave to 145° C. The reaction mixture was stirred at 145° C. for 17 hours (during the reaction, a pressure of 4 to 5 bars resulted). After completion of the reaction, cooling to 90° C. took place. 1 kg of sodium hydroxide (50 weight %) was added to adjust to alkaline and in a nitrogen atmosphere, 0.5 kg of Raney nickel were added. The suspension was heated to 100° to 110° C. and at this temperature, hydrogen was pressed on with 7 bars. Hydrogenation was carried out for 16 hours and then the mixture was cooled to 70° C. and the catalyst was separated with a pressure filter. The pyridine-3-sulfonic acid was isolated as in Example 4 and purified.

EXAMPLE 6

252 g of sodium sulfite were dissolved in 700 of water and to this solution were added 129.6 g of raw 3-chloro-pyridine-N-oxide. In a nitrogen atmosphere, the reaction mixture was heated to 145° C. and stirred for 17 hours at this temperature. Subsequent cooling to 60° C. took place and 35 ml of ethanol, 35 g of sodium hydroxide (50%) and 14 g of Raney nickel were added. The suspension was again heated to 100° C. and hydrogenated at 7 bars for 6 hours. Cooling to 50° C. took place and the catalyst was filtered off.

Sulfite still contained in the reaction solution was oxidized with 30 ml of hydrogen peroxide (70%) and at this point, approximately 400 ml of water were distilled from the reaction mixture in vacuo and 400 ml of glycol were added. Additional water was distilled off until the liquid phase temperature had risen to 100° C. Without further distillation, the temperature was increased to 130° C. by decreasing the vacuum. The hot suspension was filtered and the residue was washed with 100 ml of hot glycol. From the combined filtrate, glycol was distilled off until a residue remained which was still stirrable and which after cooling was mixted with 500 ml of concentrated hydrochloric acid and stirred for one hour at 35° C. Sodium chloride precipitate was filtered off and washed with 100 ml of concentrated hydrochloric acid. The filtrates were purified and concentrated to the limit of stirrability. Then, 300 ml of isopropanol were added at 80° C. The suspension was cooled to 20° C. and filtered. The filter cake was washed with 100 ml of isopropanol and the yield of the raw acid was 80 to 83%.

For further purification, the product was dissoleved in 260 ml of water and after the addition of 5 g of activated charcoal (Eponit), stirring took place for 30 minutes at 80° C. followed by filtering. From the filtrate, approximately 170 ml of water were distilled off and after cooling to 70° C., 350 ml of ethanol were added. After cooling to 20° C., the precipitated pyridine-3-sulfonic acid was filtered off and then washed with 100 ml of methanol to obtain a yield of pure pyridine-3-sulfonic acid of between 77 to 80% with a purity of 99%.

Various modifications of the process of the invention may be made without departing from the spirit or scope thereof and it is to be understood that the invention is intended to be limited only as defined in the appended claims.

What we claim is:

1. A process for the preparation of pyridine-3-sulfonic acid comprising oxidizing 3-chloro-pyridine to form 3-chloro-pyridine-N-oxide, reacting the latter with a sulfonating agent to form 3-sulfonic acid-pyridine-N-oxide and reducing the latter by hydrogenation in the presence of Raney nickel to form pyridine-3-sulfonic acid.

2. The process of claim 1 wherein the reduction is effected in an aqueous alkaline solution in the presence of sulfite ions and sulfonation by-products.

3. The process of claim 1 wherein sulfite ions are removed before hydrogenation by acid addition without removal of sulfonation by-products.

* * * * *